United States Patent [19]

Dietz et al.

[11] Patent Number: 4,986,851

[45] Date of Patent: Jan. 22, 1991

[54] PIGMENT DISPERSIONS, PROCESSES FOR THEIR PREPARATION AND THEIR USE

[75] Inventors: Erwin Dietz, Kelkheim; Albert Münkel; Ferdinand Memmel, both of Frankfurt am Main, all of Fed. Rep. of Germany

[73] Assignee: Hoechst Aktiengesellschaft, Frankfurt, Fed. Rep. of Germany

[21] Appl. No.: 327,332

[22] Filed: Mar. 22, 1989

Related U.S. Application Data

[63] Continuation of Ser. No. 81,833, Aug. 5, 1987, abandoned.

[30] Foreign Application Priority Data

Aug. 9, 1986 [DE] Fed. Rep. of Germany ....... 3627023

[51] Int. Cl.$^5$ .................... C08K 5/42; C08K 5/51; C09D 11/00
[52] U.S. Cl. .................... 106/503; 106/23; 252/128; 252/174.16; 252/554; 252/555; 252/556; 252/558
[58] Field of Search ............. 106/503, 23; 252/128, 252/174.16, 554, 555, 556, 558

[56] References Cited

U.S. PATENT DOCUMENTS 3,869,412  3/1975  Waag ................. 252/174.16
4,156,616  5/1979  Dietz et al. ............. 106/503

FOREIGN PATENT DOCUMENTS 53-113631  10/1978  Japan .
2133414  7/1984  United Kingdom .

*Primary Examiner*—Prince E. Willis
*Assistant Examiner*—Christine A. Skane
*Attorney, Agent, or Firm*—Connolly & Hutz

[57] ABSTRACT

The invention relates to pigment dispersions which contain, as dispersing agents, alkylglycol ether-sulfates and phosphoric acid esters of fatty alcohols and oxyethylated fatty alcohols and which are suitable for pigmenting aqueous media, in particular cosmetic articles, such as soaps, fingerpaint colors and washing powders.

14 Claims, No Drawings

PIGMENT DISPERSIONS, PROCESSES FOR THEIR PREPARATION AND THEIR USE

CROSS REFERENCE TO RELATED APPLICATION

This application is a continuation of U.S. application Ser. No. 07/081,833, filed Aug. 5, 1987, now abandoned.

The invention relates to pigment dispersions, their preparation and their use for pigmenting aqueous media, in particular cosmetic articles.

A large number of pigment dispersions which contain anionic and/or nonionic auxiliaries as dispersing agents are known for the most diverse fields of use. These auxiliaries are as a rule alkylaryl compounds or oxyalkylation and/or sulfation products thereof. These dispersing agents, which are outstandingly suitable for dispersing solids in aqueous systems, have only a limited biological degradability and are therefore unsuitable for use in the cosmetics sector and cleaning agent sector. Skin and mucosa intolerances as a rule also cannot be excluded with these products. Pigment dispersions which contain, as dispersing agents, substances which are used as base materials for cosmetics and pharmacy, in addition to containing suitable coloring agents for the cosmetics sector, are therefore desired for pigmenting cosmetic articles.

The present invention relates to pigment dispersions consisting of (A) 10 to 80% by weight, preferably 20 to 70% by weight, of a pigment, (B) 2 to 20% by weight, preferably 3 to 15% by weight, of one or more alkylglycol ether-sulfates of the general formula (I)

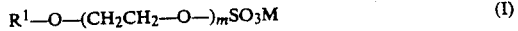

$$R^1-O-(CH_2CH_2-O-)_mSO_3M \qquad (I)$$

in which
$R^1$ represents an alkyl or alkenyl radical with 6 to 28 carbon atoms, preferably with 10 to 20 carbon atoms,
m represents an integer from 1 to 20, preferably 1 to 10, and
M represents a physiologically acceptable cation, preferably an alkali metal cation or an ammonium ion, (C) 0.1 to 10% by weight, preferably 0.3 to 5% by weight, of one or more phosphoric acid esters of the general formula (II)

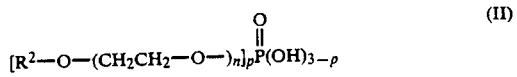

$$[R^2-O-(CH_2CH_2-O-)_n]_pP(OH)_{3-p} \qquad (II)$$

in which the radicals $R^2$ independently of one another each represent an alkyl or alkenyl radical with 4 to 28 carbon atoms, preferably 8 to 20 carbon atoms, the symbols n independently of one another each represent an integer from 0 to 10, preferably 0 to 5, and p represents an integer from 1 to 3, (D) 0 to 60% by weight, preferably 3 to 50% by weight and in particular 5 to 40% by weight, of a physiologically acceptable water retention agent, (E) 0 to 5% by weight, preferably 0 to 3% by weight, of customary additives and (F) 0 to 80% by weight, preferably 10 to 60% by weight, of water, the sum of the constituents (A), (B), (C), (D), (E) and (F) present making up 100% by weight of the pigment dispersion.

The abovementioned constituents (B), (C) and (D) of the pigment dispersions according to the invention are given in the CTFA list (Cosmetic Toiletry Fragrance Association) in the Cosmetic Ingredient Dictionary. The alkylglycol ether-sulfates listed under (B) are used in shampoos, bubble and shower baths and other body cleaning agents and are 98% degradable according to the methylene blue method. The phosphoric acid esters listed under (C) are used in cosmetics as emulsifiers in creamy oil-in-water emulsions.

If the auxiliary mentioned under (C) is omitted in the preparation of the pigment dispersions, extreme foaming of the aqueous dispersion is to be found on dispersion under the customary aqueous conditions, for example with stirred bead mills. Foaming leads, inter alia, to a drastic reduction in the grinding performance of the stirred bead mills.

Surprisingly, by the presence of one of the phosphoric acid esters listed under (C) in the preparation of the pigment dispersions according to the invention, it is possible to suppress the excessive foaming to a normal degree.

The aqueous pigment dispersions obtained after dispersion can be incorporated as such into use media or also dried and further processed as powders.

The pigment dispersions according to the invention have a surprisingly high tinctorial strength and good storage stability. Constituent (C) does not, at the same time, have an adverse influence on the above technological properties of the pigment dispersions.

Pigment dispersions according to the invention which are of particular interest are those in which constituent (B) is chosen from the following compounds: alkali metal salts and ammonium salts, preferably sodium salts, of alkyl- or alkenylmonoglycol ether-sulfates or alkyl- or alkenyloligoglycol ether-sulfates with up to 20, preferably up to 10 and in particular 2 or 3, oxyethylene units and with alkyl radicals or alkenyl radicals such as hexyl, heptyl, octyl, nonyl, decyl, undecyl, dodecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, 2-methyl-pentyl, 2-ethyl-hexyl, 2-propylheptyl, 2-butyl-octyl, 2-pentyl-nonyl, 2-hexyl-decyl, 2-heptyl-undecyl, 2-octyl-dodecyl, 2-nonyl-tridecyl, 2-decyl-tetradecyl, 2-undecyl-pentadecyl, 2-dodecyl-hexadecyl, 10-undecenyl, 9c-octadecenyl, 9t-octadecenyl, 9c,12c-octadecadienyl, 9c,12c,15c-octadecatrienyl, 9c-eicosenyl, 5,8,11,14-eicosatetraenyl, 13c-docosenyl and 13t-docosenyl, preferably decyl, dodecyl, tetradecyl, hexadecyl, octadecyl and 9c-octadecenyl; particularly preferred constituents (B) of the pigment dispersions according to the invention are the sodium salts of oleyltriglycol ether-sulfate, cetyltriglycol ether-sulfate, tetradecyltriglycol ether-sulfate, stearyltriglycol ether-sulfate, lauryltriglycol ether-sulfate, lauryldiglycol ether-sulfate, tetradecyldiglycol ethersulfate, cetyldiglycol ether-sulfate, oleyldiglycol ether-sulfate, stearyldiglycol ether-sulfate and mixtures of the compounds mentioned, in particular lauryldiglycol ether-sulfate and tetradecyldiglycol ether-sulfate. The pigment dispersions according to the invention contain as constituent (C) orthophosphoric acid esters of alkanols or alkenols such as butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, pentacosanol, hexacosanol, heptacosanol, octacosanol, 2-methyl-pentanol, 2-ethyl-hexanol, 2-propyl-heptanol, 2-butyl-octanol, 2-pentyl-nonanol, 2-hexyl-decanol, 2-heptyl-undecanol, 2-octyl-dodecanol, 2-nonyl-tridecanol, 2-decyl-tetradecanol, 3-undecyl-pentadecanol, 2-dodecyl-hexadecanol, 10-undecenol, 9c-octadecenol, 9t-octadecenol, 9c,12c-octadecadienol, 9c,12c,15c-octadecatrienol, 9c-eicosenol, 5,8,11,14-eicosatetraenol, 13c-docosenol and 13t-docosenol which are optionally oxyethylated with up to 10 mol of ethylene oxide, preferably with up to 5 mol of ethylene oxide, preferably mono-, di- and tri-ortho-phosphoric acid esters of octanol, decanol, dodecanol, tetradecanol, hexadecanol, octadecanol, 9c-octadecenol, eicosanol and oxyethylates of the alcohols with up to 5 oxyethylene units, as well as mixtures of the orthophosphoric acid esters. Particularly preferred phosphoric acid esters of the above-mentioned formula (II) are mono-, di- and tri-(lauryltetraglycol ether) orthophosphates, mono-, di and tri-(tetradecyltetraglycol ether) orthophosphates, mono-, di- and tri-(stearyltetraglycol ether) orthophosphates, mono-, di- and tri-(cetyltetraglycol ether) orthophosphates, mono-, di- and tri-(octadecenylglycol ether) orthophosphates and, in particular, mono-, di- and tri-(octadecenyl) orthophosphates.

Water retention agents of the sugar-alcohol type, such as sorbitol, mannitol, adonitol, dulcitol, erythritol, xylitol and, in particular, glycerol, or glycols, such as 1,2-propanediol, are preferably suitable as constituent (D) of the pigment dispersions according to the invention.

The pigment dispersions according to the invention can also contain minor amounts of other auxiliaries customary for the cosmetics sector, such as antisettling agents, wetting agents and preservatives (see constituent (E)).

The pigment dispersions according to the invention contain pigments as constituent (A), the term pigment here being understood as coloring agents which are largely insoluble in water and in organic solvents, such as inorganic pigments, pigment fillers and organic pigments, as long as these are permitted in cosmetics legislation.

Examples of suitable inorganic pigments or fillers are white pigments and colored pigments, such as titanium dioxides, iron oxides and carbon black, in particular Pigment Yellow 42/43 (C.I. No. 77492), Pigment Brown 6/7 (C.I. No. 77491), Pigment Black 11 (C.I. No. 77499) and Pigment White 6 (C.I. No. 77891).

Suitable organic pigments which may be mentioned are, inter alia, pigments from the azo, copper phthalocyanine, indigo, anthraquinone, dioxazine and quinacridone pigment group, preferably Pigment Red 4 (C.I. No. 12085), Pigment Red 181 (C.I. No. 73360), Pigment Red 5 (C.I. No. 12490), Pigment Red 68 (C.I. No. 15525), Pigment Green 7 (C.I. No. 74260), Pigment Red 3 (C.I. No. 12120), Pigment Red 12 (C.I. No. 12385) and Pigment Blue 15 (C.I. No. 74160), but also, for example, Pigment Yellow 1 (C.I. No. 11680), Pigment Orange 43 (C.I. No. 71105), Pigment Red 2 (C.I. No. 12310), Pigment Red 7 (C.I. No. 12420), Pigment Red 8 (C.I. No. 12335), Pigment Red 10 (C.I. No. 12440), Pigment Violet 23 (C.I. No. 51319), Pigment Red 209 (C.I. No. 73905), Pigment Yellow 12 (C.I. No. 21090), Pigment Yellow 13 (C.I. No. 21100), Pigment Yellow 83 (C.I. No. 21108), Pigment Orange 34 (C.I. No. 21115), Pigment Red 9 (C.I. No. 12460) and Pigment Red 112 (C.I. No. 12370), Pigment Orange 4 (C.I. No. 12459), Pigment Orange 1 (C.I. No. 11725), Pigment Red 146 (C.I. No. 12485), Pigment Red 171 (C.I. No. 12512), Pigment Red 175 (C.I. No. 12513), Pigment Red 88 (C.I. No. 73312), Pigment Red 209 (C.I. No. 73905), Pigment Red 122, Pigment Reds 144, 166, 170 and 188, Pigment Orange 13 (C.I. No. 21110), Pigment Orange 20 (C.I. No. 77199), Pigment Yellow 2 (C.I. No. 11730), Pigment Yellow 49 (C.I. No. 11765), Pigment Yellow 97 (C.I. No. 11767), Pigment Yellow 16 (C.I. No. 20040), Pigment Yellow 17 (C.I. No. 21105), Pigment Yellow 55 (C.I. Nc. 21096), Pigment Yellow 38 (C.I. No. 77878), Pigment Yellow 36 (C.I. No. 77975), Pigment Green 8 (C.I. No. 10006), Pigment Green 10 (C.I. No. 12775), Pigment Green 37 (C.I. No. 74255), Pigment Blue 16 (C.I. No. 74100) and Pigment Blue 30 (C.I. No. 77420).

The invention also relates to the process for the preparation of the pigment dispersions according to the invention, which comprises dispersing component (A), in the form of a powder, granules or an aqueous press cake, in the presence of water and at least the other components (B) and (C) in a manner which is customary per se, subsequently admixing the other optional components (D) and/or (E) and adjusting the resulting aqueous pigment dispersion to the desired concentration with water or drying the aqueous pigment dispersion.

Preferably, components (B), (C), (D), (E) and (F) are mixed first and component (A) is stirred into the mixture taken and dispersed according to the particle hardness of the solids employed, for example using stirrers, dissolvers, rotorstator mills, bead mills, stirred bead mills, such as sand and bead mills, highspeed mixers or kneading apparatus.

Dried pigment dispersions are preferably prepared without a water retention agent (component D). Drying is here carried out in the manner customary for aqueous pigment dispersions, in particular by means of spray-drying.

The invention also relates to the use of the pigment dispersions according to the invention for pigmenting aqueous media, in particular cosmetic articles.

Pigment dispersions according to the invention have a good storage stability and a high solids content. The aqueous pigment dispersions have good rheological properties. The aqueous and dry pigment dispersions are suitable for pigmenting aqueous media, in particular cosmetic articles, such as soaps, fingerpaint colors and washing powders, and agents for decorative cosmetics, such as creams, make-up and greasepaint sticks.

In the preparation examples which follow, parts designate parts by weight; percentage data and ratios relate to the weight.

EXAMPLE 1

8 parts of a mixture of mono-, di- and tri-oleyl orthophosphate and 28 parts of a 70% aqueous solution of an alkyldiglycol ether-sulfate sodium salt (alkyl=$C_{12}$/$C_{14}$-alkyl in a ratio of about 72:28; naturally occurring), 40 parts of glycerol and 85 parts of water are taken and mixed in a grinding container After 200 parts of Pigment Yellow 3 had been stirred in using a dissolver, 1,200 parts of Siliquarzite beads ($\phi$ 1 mm) were added and the mixture was ground in a discontinuous stirred bead mill for 1 hour. The temperature of the ground material was 30° C., at a cooling water temperature of 10° C. After dilution with 39 parts of water, the ground material was separated off from the grinding bodies and deaerated. A storage-stable pigment dispersion with very good flow properties and a pigment content of 50% was obtained.

EXAMPLE 2

180 parts of Pigment Yellow 1 were dispersed in a mixture of 24 parts of the 70% aqueous solution of the alkyldiglycol ether-sulfate sodium salt from Example 1, 12 parts of a mixture of mono-, di- and tri-(alkyltetraglycol ether) orthophosphates (alkyl=$C_{12}/C_{14}$-alkyl, naturally occurring), 40 parts of sorbitol and 113 parts of water in a bead mill analogously to Example 1.

After dilution with 31 parts of water, a storage-stable pigment dispersion with good flow properties and a pigment content of 45% was obtained.

EXAMPLE 3

160 parts of Pigment Blue 15:1 (C.I. No. 74160) in a mixture of 32 parts of a 70% aqueous solution of an alkyltriglycol ether-sulfate sodium salt (alkyl=$C_{12}/C_{14}$-alkyl; synthetic), 8 parts of a mixture of mono-, di- and trioleyl orthophosphates, 80 parts of glycerol and 80 parts of water were dispersed in a bead mill analogously to Example 1. After dilution with 40 parts of water, a storage-stable pigment dispersion with good flow properties and a pigment content of 40% was obtained.

EXAMPLE 4

235 parts of Pigment Green 7 were dispersed in a mixture of 37.5 parts of the alkyldiglycol ether-sulfate sodium salt described in Example 1, 15 parts of the phosphoric acid ester described in Example 1, 125 parts of glycerol and 67.5 parts of water analogously to Example 1, and the dispersion was diluted with 20 parts of water. The viscosity of the resulting pigment dispersion was 0.83 Pas (Pas=Pascal seconds) under a shear gradient of $D=56$ $s^{-1}$.

COMPARISON EXAMPLE 1

240 parts of Pigment Green 7 were dispersed in a mixture of 37.5 parts of the alkyldiglycol ether-sulfate sodium salt described in Example 1, 125 parts of glycerol and 75 parts of water analogously to Example 1, and the dispersion was then diluted with 22.5 parts of water. The viscosity of the resulting pigment dispersion was 0.85 Pas under a shear gradient of $D=56$ $s^{-1}$. Marked foaming occurred during dispersion in the bead mill.

COMPARISON EXAMPLE 2

230 parts of Pigment Green 7 were dispersed in a mixture of 30 parts of an addition product of nonylphenol and 30 mol of ethylene oxide, 150 parts of glycerol and 80 parts of water analogously to Example 1. After dilution with 35 parts of water, the viscosity of the resulting pigment dispersion was 0.82 Pas under a shear gradient of $D=56$ $s^{-1}$.

Foaming Test

In order to test the foaming properties under conditions in practice and under the preparation conditions, the pigment preparations from Example 4, Comparison Example 1 and Comparison Example 2 were stirred intensively under constant conditions. The stirring time with a sawtooth dissolver (n=5,000 minute$^{-1}$; amount of product 200 g; disc diameter 30 mm) was in each case 30 minutes. The pigment dispersions had a comparable viscosity. The density of the dispersion after stirring was measured as a measure of foaming and was compared with the density after deaeration of the dispersion. The densities measured are listed in Table 1, together with the viscosities of the deaerated pigment dispersions.

TABLE 1

| Dispersion | Viscosity $D=56$ $s^{-1}$ (Pas) | Density deaerated (g × cm$^{-3}$) | Density after stirring (g × cm$^{-3}$) |
|---|---|---|---|
| Example 4 | 0.83 | 1.45 | 0.57 |
| Comparison Example 1 | 0.85 | 1.47 | 0.35 |
| Comparison Example 2 | 0.82 | 1.40 | 0.56 |

As can be seen in Table 1, the dispersion from Comparison Example 1 tends towards extreme foaming without the phosphoric acid ester, which is shown by the low density after stirring. Comparison Example 2, which contains a commercially available nonionic dispersing agent which is only inadequately biologically degradable, is comparable to Example 4 according to the invention in respect of the tendency to foam.

USE EXAMPLES 100 parts of soap base are taken in a kneader, 0.2 part of the pigment preparation described in Examples 1, 2, 3 or 4 and 50 parts of water are added and the mixture is kneaded for 30 minutes. The colored soap base is then warmed in an extruder at 40° C., and after discharge is pressed into a mold. Deeply colored, transparent moldings are obtained. Opaque colorations are obtained if 2 parts of titanium dioxide are kneaded in additionally to the pigment preparation.

We claim:
1. A pigment dispersion consisting of
(A) 10 to 80% by weight of a pigment,
(B) 2 to 20% by weight of one or more alkylglycol ether-sulfates of the formula (I)

$$R^1-O-(CH_2CH_2-O-)_mSO_3M \qquad (I)$$

in which
$R^1$ represents an alyl or alkenyl radical with 6 to 28 carbon atoms,
m represents an integer from 1 to 20 and
M represents a physiologically acceptable cation,
(C) 0.1 to 10% by weight of one or more phosphoric acid esters of the formula (II)

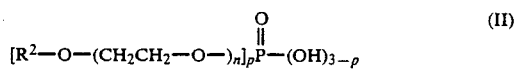

$$[R^2-O-(CH_2CH_2-O-)_n]_pP(=O)-(OH)_{3-p} \qquad (II)$$

in which
the radicals $R^2$ independently of one another represent an alkyl or alkenyl radical with 4 to 28 carbon atoms,
the symbols n independently of one another represent an integer from 0 to 10 and
p represents an integer from 1 to 3,
(D) 3 to 60% by weight of a physiologically acceptable sugar-alcohol water retention agent, including glycerol, (E) 0 to 5% by weight of customary additives selected from the group consisting of preservatives, and antisettling and wetting agents, and (F) 0 to 80% by weight of water, the sum of the constituents (A), (B), (C), (D), (E) and (F) present making up 100% by weight of the dispersion.

2. A pigment dispersion as claimed in claim 1, which contains (A) 20 to 70% by weight of a pigment, (B) 3 to 15% by weight of one or more alkylglycol ether-sulfates of the formula (I) mentioned in claim 1, (C) 0.3 to 5% by weight of one or more phosphoric acid esters of the formula (11) mentioned in claim 1, (D) 3 to 50% by weight of the water retention agent as set forth in claim 1, (E) 0 to 3% by weight of the customary additives as set forth in claim 1, (F) 10 to 60% by weight of water, the sum of the constituents (A) to (F) present making up 100% by weight of the dispersion.

3. A pigment dispersion as claimed in claim 1 which contains one or more alkylglycol ethersulfates of the formula (I) mentioned in claim 1, in which $R^1$ represents an alkyl or alkenyl radical with 10 to 20 carbon atoms, m represents a number from 1 to 10 and M represents an alkali metal cation or the ammonium ion.

4. A pigment dispersion as claimed in claim 3, wherein $R^1$ represents an alkyl or alkenyl radical with 12 to 18 carbon atoms and m represents 2 or 3.

5. A pigment dispersion as claimed in claim 4, which contains at least one alkylglycol ether-sulfate selected from the group consisting of lauryldiglycol ether-sulfate, lauryltriglycol ether-sulfate, tetradecyldiglycol ether-sulfate, tetradecyltriglycol ether-sulfate, cetyldiglycol ether-sulfate, cetyltriglycol ether-sulfate, stearyldiglycol ethersulfate, stearyltriglycol ether-sulfate, oleyldiglycol ether-sulfate and oleyltriglycol ether-sulfate 6. A pigment dispersion as claimed in claim 1, which contains one or more phosphoric acid esters of the formula (II) given in claim 1 in which $R^2$ represents an alkyl or alkenyl radical with 8 to 20 carbon atoms, n represents 0, 1, 2, 3, 4 or 5 and p represents 1, 2 or 3.

7. A pigment dispersion as claimed in claim 6, wherein $R^2$ represents an alkyl or alkenyl radical with 12 to 18 carbon atoms.

8. A pigment dispersion as claimed in claim 7, wherein $R^2$ represents lauryl, tetradeyl, cetyl, stearyl or oleyl.

9. A pigment dispersion as claimed in claim 7, which contains at least one phosphoric acid ester selected from the group consisting of mono-, di- and tri-(lauryltetraglycol ether) orthophosphate, mono-, di- and tri-(tetradecyltetraglycol ether) orthophosphate, mono-, di and tri-(cetyltetragycol ether) orthophosphate, mono-, di- and tri-(stearyltetraglycol ether) orthophosphate, mono-, di- and tri-(oleylglycol ether) orthophosphate and mono-, di- and tri-(oleyl) orthophosphate.

10. A pigment dispersion as claimed in claim 1, wherein the physiologically acceptable water retention agent (constituent (D)) is selected from the group consisting of glycerol, sorbitol, mannitol, adonitol, dulcitol, erythritol, xylitol and 1,2-propandiol.

11. A pigment dispersion as claimed in claim 2, which contains at least one alkylglycol ether-sulfate of the formula $R^1-O-(CH_2CH_2O)_mSO_3M$ in which $R^1$ represents an alkyl or alkenyl radical with 12 to 18 carbon atoms, m is 2 or 3 and M is an alkali metal cation or ammonium, and which contains at least one phosphoric ester of the formula $[R^2-O-(CH_2CH_2O)_n]_pPO(OH)_{3-p}$ in which $R^2$ represents an alkyl or alkenyl radical with 12 to 18 carbon atoms, n is an integer from 0 to 10 and p is 1, 2 or 3.

12. A method of pigmenting in an aqueous medium, which comprises the step of incorporation a pigment dispersion as defined in claim 1 into the aqueous medium.

13. Method as claimed in claim 12, wherein the aqueous medium is an cosmetic article or is processed into an cosmetic article.

14. Method as claimed in claim 13, wherein the cosmetic article is a soap, a fingerpaint color or a washing powder.

* * * * *